United States Patent
Kotani et al.

(10) Patent No.: US 12,396,670 B2
(45) Date of Patent: Aug. 26, 2025

(54) SEAT RECLINING POSITION CONTROL DEVICE

(71) Applicant: DENSO CORPORATION, Kariya (JP)

(72) Inventors: Ayako Kotani, Kariya (JP); Yukari Itou, Kariya (JP); Akihiro Hayashi, Kariya (JP); Makiko Sugiura, Kariya (JP); Kunihiko Chiba, Kariya (JP)

(73) Assignee: DENSO CORPORATION, Kariya (JP)

( * ) Notice: Subject to any disclaimer, the term of this patent is extended or adjusted under 35 U.S.C. 154(b) by 236 days.

(21) Appl. No.: 18/158,755

(22) Filed: Jan. 24, 2023

(65) Prior Publication Data

US 2023/0166638 A1 Jun. 1, 2023

Related U.S. Application Data

(63) Continuation of application No. PCT/JP2021/027805, filed on Jul. 27, 2021.

(30) Foreign Application Priority Data

Aug. 7, 2020 (JP) .................................. 2020-134990

(51) Int. Cl.
*G08G 1/16* (2006.01)
*A47C 1/024* (2006.01)
(Continued)

(52) U.S. Cl.
CPC .............. *A61B 5/18* (2013.01); *B60N 2/0022* (2023.08); *B60N 2/0024* (2023.08);
(Continued)

(58) Field of Classification Search
CPC ...... B60N 2/22; B60N 2/0027; B60N 2/0273; B60N 2/0025; B60N 2/003; B60N 2/02;
(Continued)

(56) References Cited

U.S. PATENT DOCUMENTS

| 2010/0207434 A1* | 8/2010 | Kurrasch ............. A47C 31/126 |
| | | 297/217.2 |
| 2016/0159251 A1 | 6/2016 | Ebina et al. |

(Continued)

FOREIGN PATENT DOCUMENTS

| JP | 2006008098 A | 1/2006 |
| JP | 2006244343 A | 9/2006 |

(Continued)

*Primary Examiner* — Khoi H Tran
*Assistant Examiner* — Alyse Tramanh Tran
(74) *Attorney, Agent, or Firm* — Harness, Dickey & Pierce, P.L.C.

(57) ABSTRACT

A seat reclining position control device includes: a seat on which an occupant of a vehicle sits; an adjustment part configured to adjust an angle of a backrest of the seat; a sleep state detection unit configured to detect a sleep state of the occupant; a control unit that operates the adjustment unit to control the angle; and a vehicle interior detection unit configured to detect a vehicle interior state of the vehicle. The control unit implements a seat angle control to adjust the angle of the backrest for the occupant in the sleep state based on the vehicle interior state to a suitable sleeping angle suitable for sleeping when the sleep state detection unit detects the sleep state of the occupant.

19 Claims, 7 Drawing Sheets

(51) Int. Cl.
*A61B 5/18* (2006.01)
*B60N 2/00* (2006.01)
*B60N 2/02* (2006.01)
*B60N 2/06* (2006.01)
*B60N 2/16* (2006.01)
*B60N 2/22* (2006.01)
*B60W 50/16* (2020.01)
*G01C 21/26* (2006.01)

(52) U.S. Cl.
CPC ......... *B60N 2/0027* (2023.08); *B60N 2/0252* (2013.01); *B60N 2/0273* (2023.08); *B60N 2/0278* (2023.08); *B60N 2/22* (2013.01); *B60W 50/16* (2013.01); *B60N 2/0268* (2023.08); *B60N 2/06* (2013.01); *B60N 2/16* (2013.01); *B60N 2210/24* (2023.08); *B60N 2220/10* (2023.08); *B60N 2220/20* (2023.08)

(58) Field of Classification Search
CPC ...... B60N 2/0268; B60N 2/99; B60N 2/0252; B60N 2/12; B60N 2/18; B60N 2/838; B60N 2210/24; B60N 2/002; B60N 2/0023; B60N 2/0024; B60N 2/0029; B60N 2/0256; B60N 2/2222; B60N 2/3015; B60N 2/64; B60N 2/0278; B60N 2/0022; B60W 40/08; B60W 2040/0872; B60W 2040/0827; B60W 2540/223; B60W 50/16; A61B 5/18
See application file for complete search history.

(56) References Cited

U.S. PATENT DOCUMENTS

| | | | |
|---|---|---|---|
| 2018/0015825 A1* | 1/2018 | Nania | G06V 20/597 |
| 2020/0122639 A1* | 4/2020 | Ito | G01C 21/3697 |
| 2020/0361283 A1* | 11/2020 | Suzuki | B60H 1/00742 |
| 2024/0075851 A1* | 3/2024 | Roy | G05D 1/43 |

FOREIGN PATENT DOCUMENTS

| | | | |
|---|---|---|---|
| JP | 2008200486 A | | 9/2008 |
| JP | 2010068941 A | | 4/2010 |
| JP | 2010083297 A | | 4/2010 |
| JP | 2013195351 A | * | 9/2013 |
| JP | 2015067140 A | * | 4/2015 |
| JP | 2019142356 A | | 8/2019 |
| WO | WO-2015011866 A1 | | 1/2015 |

* cited by examiner

SEAT RECLINING POSITION CONTROL DEVICE

CROSS REFERENCE TO RELATED APPLICATION

The present application is a continuation application of International Patent Application No. PCT/JP2021/027805 filed on Jul. 27, 2021, which designated the U.S. and claims the benefit of priority from Japanese Patent Application No. 2020-134990 filed in Japan on Aug. 7, 2020. The entire disclosures of all of the above applications are incorporated herein by reference.

TECHNICAL FIELD

The present disclosure relates to a seat reclining position control device.

BACKGROUND

A seat reclining position control device has a detector configured to detect a drowsiness of an occupant of a vehicle based on biological information such as pulse wave data or heart rate data of the occupant. When the occupant becomes drowsy, the seat back is reclined to a position suitable for falling asleep.

SUMMARY

A seat reclining position control device includes: a seat on which an occupant of a vehicle sits; an adjustment part configured to adjust an angle of a backrest of the seat; a sleep state detection unit configured to detect a sleep state of the occupant; a control unit configured to operate the adjustment unit to control the angle; and a vehicle interior detection unit configured to detect a vehicle interior state of the vehicle. The control unit implements a seat angle control to adjust the angle of the backrest for the occupant in the sleep state based on the vehicle interior state to a suitable sleeping angle suitable for sleeping when the sleep state detection unit detects the sleep state of the occupant.

DETAILED DESCRIPTION

Figure 1:
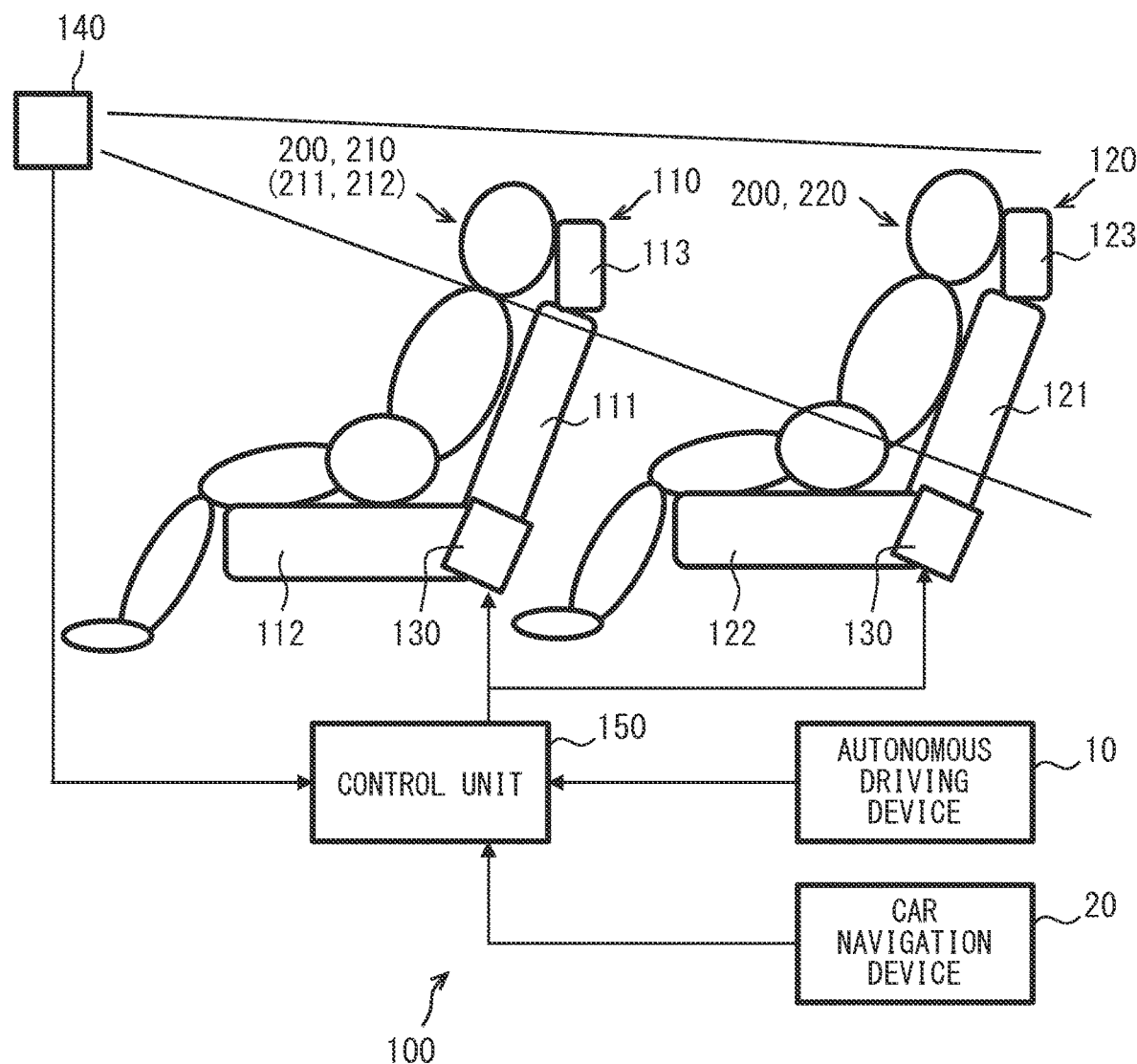
FIG. 1 is an explanatory diagram showing a seat reclining position control device according to a first embodiment.

To begin with, examples of relevant techniques will be described. A seat reclining position control device (sleep onset device) detects a drowsiness based on biological information such as pulse wave data or heart rate data of the occupant of the vehicle. When the drowsiness state is detected, the controller causes a predetermined in-vehicle device to perform an operation suitable for sleep of the occupant. As the in-vehicle device, for example, there is a seat reclining device. When the occupant becomes drowsy, the seat back is reclined to a position (angle) suitable for falling asleep.

However, the seat reclining control is performed based only on whether or not the occupant is drowsy. Nothing is taken into account, other than the drowsiness state of the occupant. A state of another occupant is not taken into consideration in the seat reclining control.

For example, depending on the posture of a drowsy occupant, reclining the seat may cause the occupant to move in an unintended direction or receive a rebound, which may cause discomfort to the occupant. Further, when there are passengers other than the drowsy occupant (to be targeted) in the rear seat, if the seat for the drowsy occupant is suddenly reclined, the other passengers feel uncomfortable.

The present disclosure provides a seat reclining position control device that can perform a seat angle control without causing discomfort to a target occupant and the other occupant.

A seat reclining position control device includes: a seat on which an occupant of a vehicle sits; an adjustment part configured to adjust an angle of a backrest of the seat; a sleep state detection unit configured to detect a sleep state of the occupant; a control unit that operates the adjustment unit to control the angle; and a vehicle interior detection unit configured to detect a vehicle interior state of the vehicle. The control unit implements a seat angle control to adjust the angle of the backrest for the occupant in the sleep state based on the vehicle interior state to a suitable sleeping angle suitable for sleeping when the sleep state detection unit detects the sleep state of the occupant.

Accordingly, the seat angle control is performed for the sleeping occupant based on the sleeping state of the occupant and the vehicle interior state detected by the vehicle interior detection unit. Therefore, it is possible to control the seat angle without giving discomfort to the sleeping occupant and the other occupant.

Hereinafter, embodiments for implementing the present disclosure will be described referring to drawings. In each embodiment, portions corresponding to the elements described in the preceding embodiments are denoted by the same reference numerals, and redundant explanation thereof may be omitted. When only a part of a configuration is described in an embodiment, the other preceding embodiments can be applied to the other parts of the configuration. It may be possible not only to combine parts the combination of which is explicitly described in an embodiment, but also to combine parts of respective embodiments the combination of which is not explicitly described if any obstacle does not especially occur in combining the parts of the respective embodiments.

First Embodiment

A seat reclining position control device 100 of the first embodiment will be described with reference to FIGS. 1 to 5. The seat reclining position control device 100 is mounted in a vehicle, for controlling an angle of a backrest 111, 121 of a front seat 110 or a rear seat 120, as a seat angle control, for example, for an occupant 200 in a sleeping state. The occupant 200 includes a front seat occupant 210 and a rear seat occupant 220.

The vehicle is, for example, a five-passenger car, and the occupant is a driver 211 alone or the driver 211 and the other passengers (at least one passenger). The vehicle may include an autonomous driving device 10 and/or a car navigation device 20.

The autonomous driving device 10 can implement automatic driving levels 1 to 5 based on the driving state of the vehicle, the driving environment (the road on which the vehicle is traveling, the surrounding environment), and the like. Automatic driving level 1 allows the autonomous driving device 10 to support either steering operation or acceleration/deceleration operation. Automatic driving level 2 allows the autonomous driving device 10 to support both the steering operation and the acceleration/deceleration operation. Automatic driving level 3 allows the autonomous driving device 10 to perform all operations in a specific place, but the driver 211 operates in an emergency. Automatic driving level 4 allows the autonomous driving device 10 to perform all operations in place of driving by the driver 211 at a specific place, and the driver 211 needs to drive after passing the specific place. Automatic driving level 5 allows the autonomous driving device 10 to perform all operations instead of driving by the driver 211, regardless of location.

The car navigation device 20 grasps the position of the vehicle by GPS (Global Positioning System), displays the result on the map screen, and guides the user to the desired destination.

As shown in FIG. 1, the seat reclining position control device 100 includes a front seat 110, a rear seat 120, an adjustment unit 130, a camera 140, and a control unit 150.

The front seat 110 includes two seats for the front seat occupant 210 (such as the driver 211 and the front passenger 212). Each front seat 110 is provided with a backrest 111, a seat portion 112 and a headrest 113. The front seat 110 has a reclining function of the backrest 111 and a position adjusting function of the seat portion 112. The front seat 110 corresponds to a seat of the present disclosure.

The rear seat 120 includes three seats for the rear seat occupant 220. Each rear seat 120 is provided with a backrest 121, a seat portion 122 and a headrest 123. The rear seat 120 has a function of reclining the backrest 121. The rear seat 120 may correspond to a seat of the present disclosure. The backrest 121 of the rear seat 120 corresponds to a rear seat backrest of the present disclosure.

In the front seat 110 and the rear seat 120, the headrest 113, 123 can be regarded as a part of the backrest 111, 121.

The adjustment unit 130 is provided on each of the front seat 110 and the rear seat 120. The adjustment unit 130 adjusts the angle of the backrest 111, 121 (reclining function). That is, the adjustment unit 130 reclines the angle of the backrest 111, 121 for the sleeping occupant suitably for sleeping, and restores the backrest 111, 121 when the occupant wakes from sleep. The adjustment unit 130 also adjusts the position of the seat portion 112 of the front seat 110 in the up-down direction and the front-rear direction (position adjustment function). The adjustment unit 130 is controlled by the control unit 150 to change the angle of the backrest 111, 121 and adjust the position of the seat portion 112.

The camera 140 is a sleep state detection unit that detects the sleep state of the occupant 200. The camera 140 is, for example, a CCD camera, a CMOS camera, an infrared camera, or the like, and is provided at a front side on the ceiling of the vehicle. The camera 140 acquires face images of all of the occupants 200 on the front seat 110 and the rear seat 120. The camera 140 outputs the acquired face image data to the control unit 150.

The camera 140 also functions as a vehicle interior detection unit that detects the state of the vehicle interior in this embodiment. The camera 140 acquires images of the seating positions and postures of all occupants 200 on board, and outputs the acquired image data (state image data) to the control unit 150.

The control unit 150 detects an occupant in a sleeping state among the occupants 200 from the face images obtained by the camera 140. For example, when the eyelids are continuously closed for a predetermined time or longer, the control unit 150 determines that the occupant 200 is in a sleep state from the face image of the occupant 200. Further, the control unit 150 grasps the seating position, the posture, etc. of each occupant 200 from the state image obtained by the camera 140. The control unit 150 grasps the current set angles of the backrests 111, 121 and the set position of the seat portion 112 in cooperation with the adjustment unit 130.

In general, the control unit 150 determines, as the state of the vehicle interior, relative to the seat 110, 120, the angle setting conditions of the backrest 111, 121, the position setting condition of the seat portion 112, which seat the occupant 200 is seated in, which occupant 200 is in a sleep state, and the sitting posture of each occupant 200.

When the vehicle is provided with the autonomous driving device 10, the control unit 150 grasps the level (1 to 5) of automatic driving currently being executed based on the information from the autonomous driving device 10. When the vehicle is equipped with the car navigation device 20, the control unit 150 grasps the time required to reach the destination, the driving difficulty level of the current road, and navigation information such as highlight points before arriving at the destination based on the information from the car navigation device 20.

Then, the control unit 150 controls the angle adjustment of the backrest 111 (or the backrest 121) with respect to the sleeping occupant 200, taking into account the state of the vehicle interior, the automatic driving level, the navigation information, and the like.

The configuration of the seat reclining position control device 100 of the present embodiment is as described above, and the operation and effects will be described below with reference to FIGS. 2 to 5.

The control unit 150 detects an occupant 200 in a sleep state in the front seat 110 or the rear seat 120 from the face images of the occupants 200 obtained from the camera 140.

The driver 211 can be included in the occupant 200 in a sleep state. When the driver 211 is in a sleep state, for example, the vehicle is controlled by the autonomous driving device 10 at the automatic driving level 4 or 5, or the vehicle is parked or stopped in a parking lot while the driver is taking a nap. It is desired that the driver 211 be preferentially relaxed during an automatic driving or during a nap, for safe driving. The occupant 200 in a sleep state includes a passenger 212 such as rear seat occupant 220, other than the driver 211.

Figure 2:
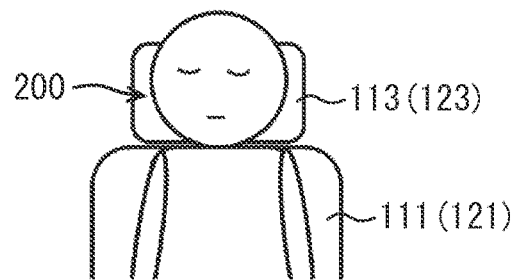
FIG. 2 is an explanatory diagram showing a straight posture of an occupant in the first embodiment.
Figure 3:
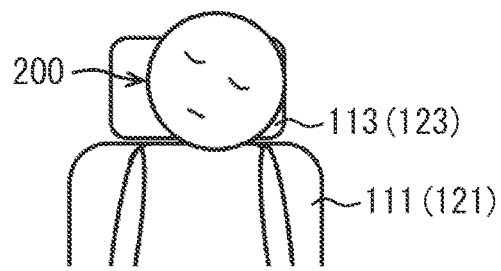
FIG. 3 is an explanatory diagram showing a slightly inclined posture of an occupant.

The control unit 150 detects the posture of the sleeping occupant 200 from the state image of the occupant 200 obtained from the camera 140. As shown in FIGS. 2 and 3, for example, when the sleeping occupant 200 is not out of the backrest 111 and/or the headrest 113, the control unit 150 reclines the backrest 111 to adjust the angle of the backrest 111 to a sleeping angle suitable for sleeping (as seat angle control). The sleeping angle of the backrest 111 is set in advance for sleeping. In case where the sleeping occupant 200 is a rear seat occupant 220, the seat angle control is performed to the backrest 121.

Figure 4:
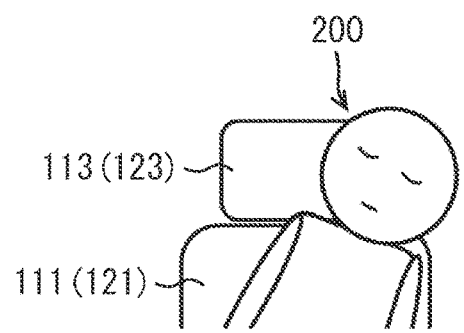
FIG. 4 is an explanatory diagram showing a case where the occupant's head is off the headrest.
Figure 5:
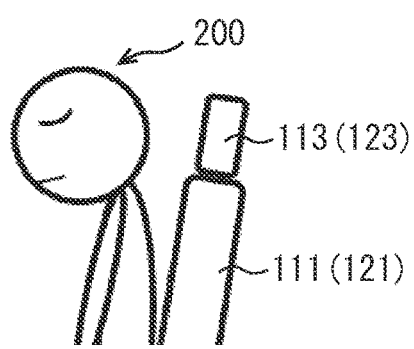
FIG. 5 is an explanatory diagram showing a case where the occupant's back is tilted forward and separated from the backrest.

As shown in FIG. 4, when the head of the sleeping occupant 200 is off the headrest 113, the control unit 150 does not execute the seat angle control. Further, the seat angle control is not executed (prohibited) when the upper body is tilted forward as shown in FIG. 5 since the back of the occupant 200 is not in contact with the backrest 111.

As described above, in the present embodiment, the control unit 150 performs the seat angle control based on the sleeping state and the seating posture of the occupant 200. As described with reference to FIG. 4, if the seat angle control is performed when the head of the occupant 200 is out of the headrest 113, the occupant 200 may move in an unintended direction (slip down from the seat). As described with reference to FIG. 5, if the seat angle control is performed when the back of the occupant 200 is not in contact with the backrest 111, the back of the occupant 200 may hit the backrest 111 by receiving a recoil due to reclining. In this embodiment, considering the above, the seat angle control is performed when the occupant 200 is not separated from the backrest 111 and/or the headrest 113, so that the occupant 200 does not feel uncomfortable.

When the sleeping occupant 200 is the driver 211 and the vehicle is automatically traveling, or when the driver 211 is taking a nap while the vehicle is parked, the control unit 150 controls the seat angle for the driver 211. Therefore, the driver 211 can have a comfortable sleep.

Second Embodiment

A seat angle control in the second embodiment will be described with reference to FIGS. 6 to 8. The configuration of the seat reclining position control device 100 is the same as that of the first embodiment. In the second embodiment, a seat angle control is performed by utilizing that the seat portion 112 of the front seat 110 is adjustable (movable) in position. The directions in which the position of the seat portion 112 can be adjusted are the up-down direction and the front-rear direction.

Figure 6:
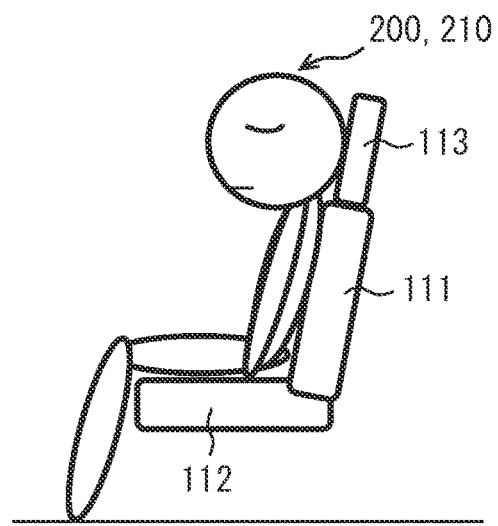
FIG. 6 is an explanatory diagram showing a state before reclining in a second embodiment.

The sleeping occupant 200 is herein assumed to be the front seat occupant 210 on the front seat 110, for example, the driver 211 or the front passenger 212 (FIG. 6).

Figure 7:
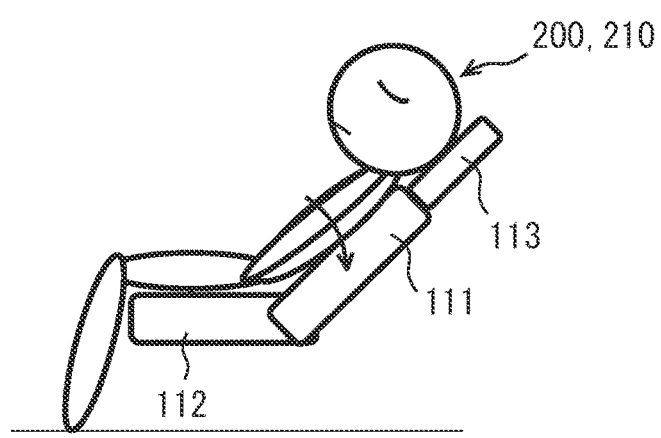
FIG. 7 is an explanatory diagram showing a state in which the backrest is reclined.
Figure 8:
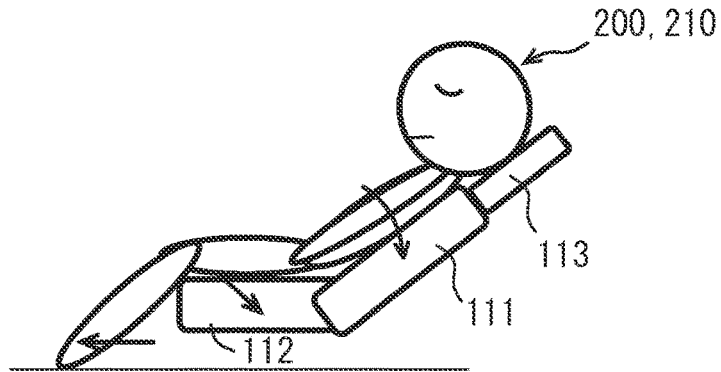
FIG. 8 is an explanatory view showing a state in which the seat portion is further moved rearward and downward.

The control unit 150 performs the seat angle control shown in FIG. 7 when there is no rear seat occupant 220 (another passenger) in the rear seat 120 at rear side of the sleeping occupant 200, as the vehicle interior state. In addition, as shown in FIG. 8, the control unit 150 moves the seat portion 112 rearward and downward.

This makes it easier for the sleeping occupant 200 to stretch his or her legs, thereby enabling sleep in a more comfortable environment. Since there is no occupant 200 in the rear seat 120, there is no rear seat occupant 220 feeling uncomfortable.

Third Embodiment

Figure 9:
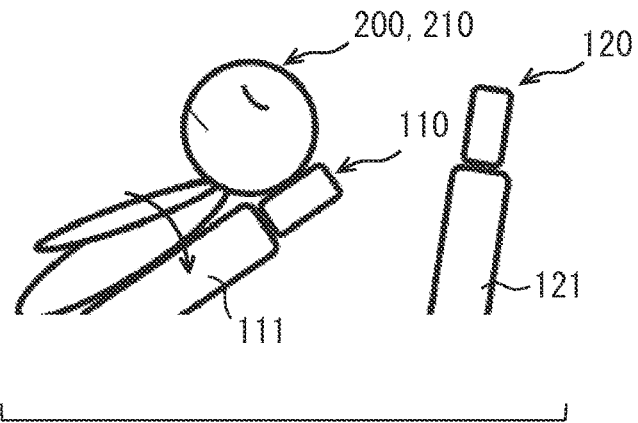
FIG. 9 is an explanatory diagram showing a reclining state when there is no passenger on the rear seat in a third embodiment.
Figure 10:
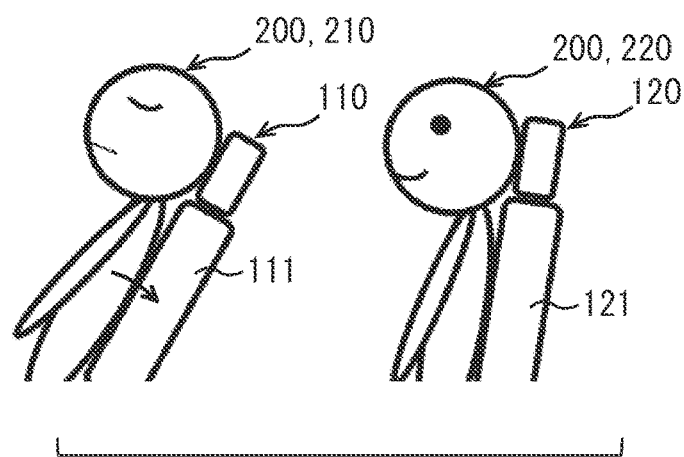
FIG. 10 is an explanatory diagram showing a reclining state when there is a passenger in the rear seat.

A seat angle control in the third embodiment will be described with reference to FIGS. 9 and 10. The configuration of the seat reclining position control device 100 is the same as that of the first embodiment. In the third embodiment, when there is a rear seat occupant 220 (another passenger) in the rear seat 120 at the rear side of the sleeping occupant 200 (front seat occupant 210) as a vehicle interior state, the control unit 150 reduces the reclining angle shown in FIG. 10, to be smaller than the normal sleeping angle shown in FIG. 9 when performing the seat angle control for the sleeping occupant 210 (front seat occupant 210).

When the control unit 150 determines that the front seat occupant 210 in a sleeping state has sufficient foot space (there is a predetermined space or more) from the control position of the seat portion 112, the control unit 150 may perform the seat angle control and move the position of the seat portion 112 forward.

Accordingly, the seat angle control for the front seat occupant 210 can be performed without impairing the comfort of the rear seat occupant 220 (so as not to make the rear seat occupant 220 uncomfortable).

Fourth Embodiment

Figure 11:
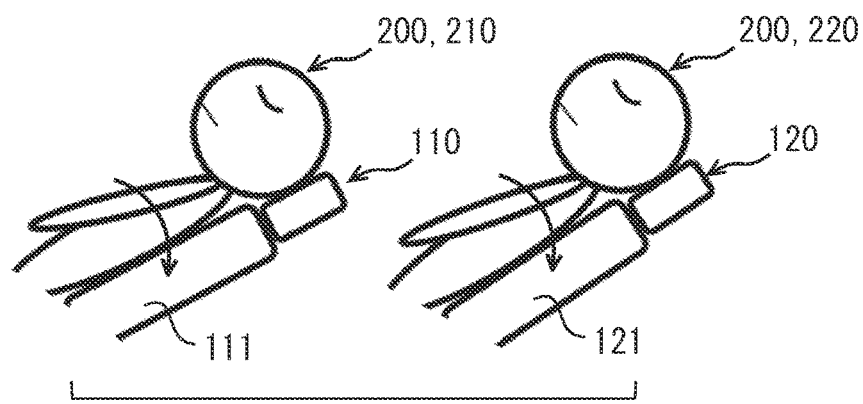
FIG. 11 is an explanatory diagram showing a reclining state when there is a passenger in a rear seat in a fourth embodiment.

FIG. 11 shows the seat angle control in the fourth embodiment. The configuration of the seat reclining position control device 100 is the same as that of the first embodiment. In the fourth embodiment, when there is a rear seat occupant 220 (another passenger) in the rear seat 120 on the rear side of the sleeping occupant 200 (front seat occupant 210) as a vehicle interior state, the control unit 150 performs the seat angle control for the sleeping occupant 210, and, as shown in FIG. 11, reclines the backrest 121 (rear seat backrest) of the rear seat 120.

When the rear seat occupant 220 is also in a sleeping state, the backrest 121 of the rear seat 120 is reclined at the same angle as the backrest 111 of the front seat 110 (FIG. 11). When the rear seat occupant 220 is awake, the reclining angle of the backrest 121 of the rear seat 120 is adjusted to be smaller than the normal sleeping angle.

Accordingly, the seat angle control for the front seat occupant 210 can be performed without impairing the comfort of the rear seat occupant 220 (so as not to make the rear seat occupant 220 uncomfortable). When the sleeping occupant 200 is the driver 211, the seat angle control (such as full reclining) is possible to prioritize the driver 211 more than in case of the third embodiment.

Fifth Embodiment

In the fifth embodiment, a seat angle control is implemented while the vehicle is automatically driven at the automatic driving level 4 or 5 by the autonomous driving device 10 and when the destination guidance is performed by the car navigation device 20. The configuration of the seat reclining position control device 100 is the same as that of the first embodiment.

The control unit 150 grasps the required time to the destination from the navigation information of the car navigation device 20. When the time required to reach the destination is shorter than a predetermined time, the control unit 150 prohibits the seat angle control for the driver 211, and permits the seat angle control for the other passengers (the passenger seat occupant 212, the rear seat occupant 220) other than the driver 211. Since the optimum time for a nap is usually 15 to 30 minutes, the predetermined time (determination time) can be set to, for example, about 5 to 10 minutes.

As a result, when the required time (distance) to the destination is short and sufficient sleep time cannot be secured, the driver 211 can be prevented from falling asleep. The other passengers can sleep comfortably by performing the seat angle control.

Sixth Embodiment

In the sixth embodiment, the procedure for adjusting the seat angle when driving on a road with a difficulty level during automatic driving will be described. The difficulty level of driving is high along, for example, city roads, roads with frequent vehicle movement, mountain roads with a series of curves, cliff roads, and the like. The control unit 150 acquires road information including the driving difficulty level from the car navigation device 20. The configuration of the seat reclining position control device 100 is the same as that of the first embodiment.

The control unit 150 prohibits the seat angle control for the driver 211, and permits the seat angle control for the other passengers (the passenger seat occupant 212, the rear seat occupant 220) other than the driver 211, when the vehicle is automatically traveling on a road with a predetermined driving difficulty level.

As a result, even during automatic driving, by prohibiting the seat angle control for the driver 211 in case a danger occurs, preparations are made so that the driver can control the driving by himself/herself at any time. The other passengers can sleep comfortably by implementing the seat angle control.

Seventh Embodiment

Figure 12:
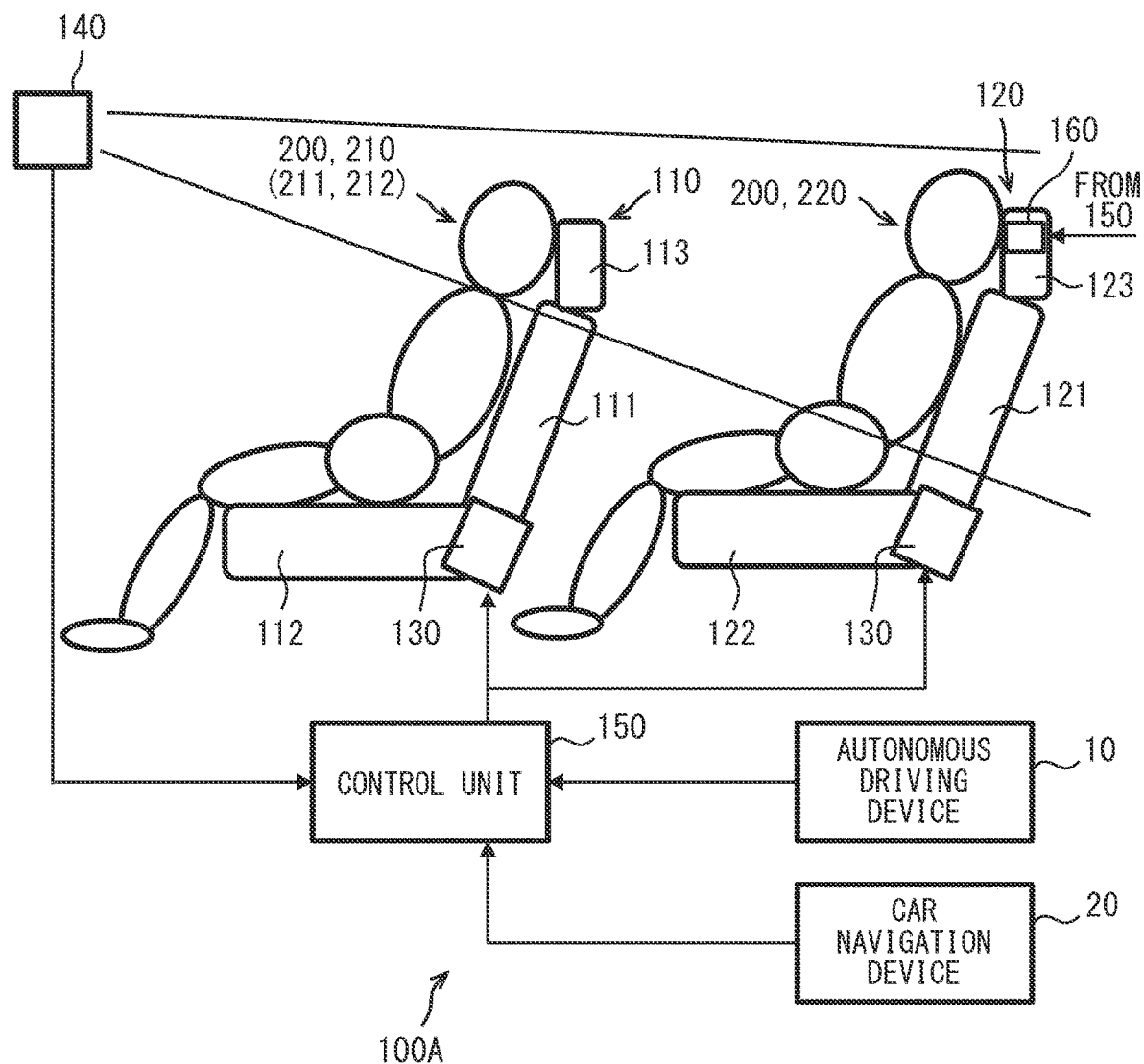
FIG. 12 is an explanatory diagram showing a seat reclining position control device according to a seventh embodiment.

FIG. 12 shows a seat reclining position control device 100A according to the seventh embodiment. The seat reclining position control device 100A includes a notification unit 160 for notifying the rear seat occupant 220. The notification unit 160 can be, for example, a directional speaker that has directivity to each rear seat occupant 220 on the rear seat 120. The notification unit 160 is provided in, for example, the headrest 123.

When the control unit 150 performs the seat angle control, if a rear seat occupant 220 (another passenger) is in the rear seat 120 at the rear side of the sleeping occupant 200 (the driver 211 or the front passenger 212) and is awake, the notification unit 160 notifies the rear seat occupant 220 in advance that the seat angle control will be performed. Specifically, the notification unit 160 notifies that, for example, "be careful as the front seat will be reclined." If the rear seat occupant 220 is in a sleep state, the control unit 150 prohibits the notification to the rear seat occupant 220.

As a result, the seat angle control can be performed without startling the rear seat occupant 220 due to the sudden seat reclining (so as not to give discomfort) by giving advance notification.

Eighth Embodiment

Figure 13:
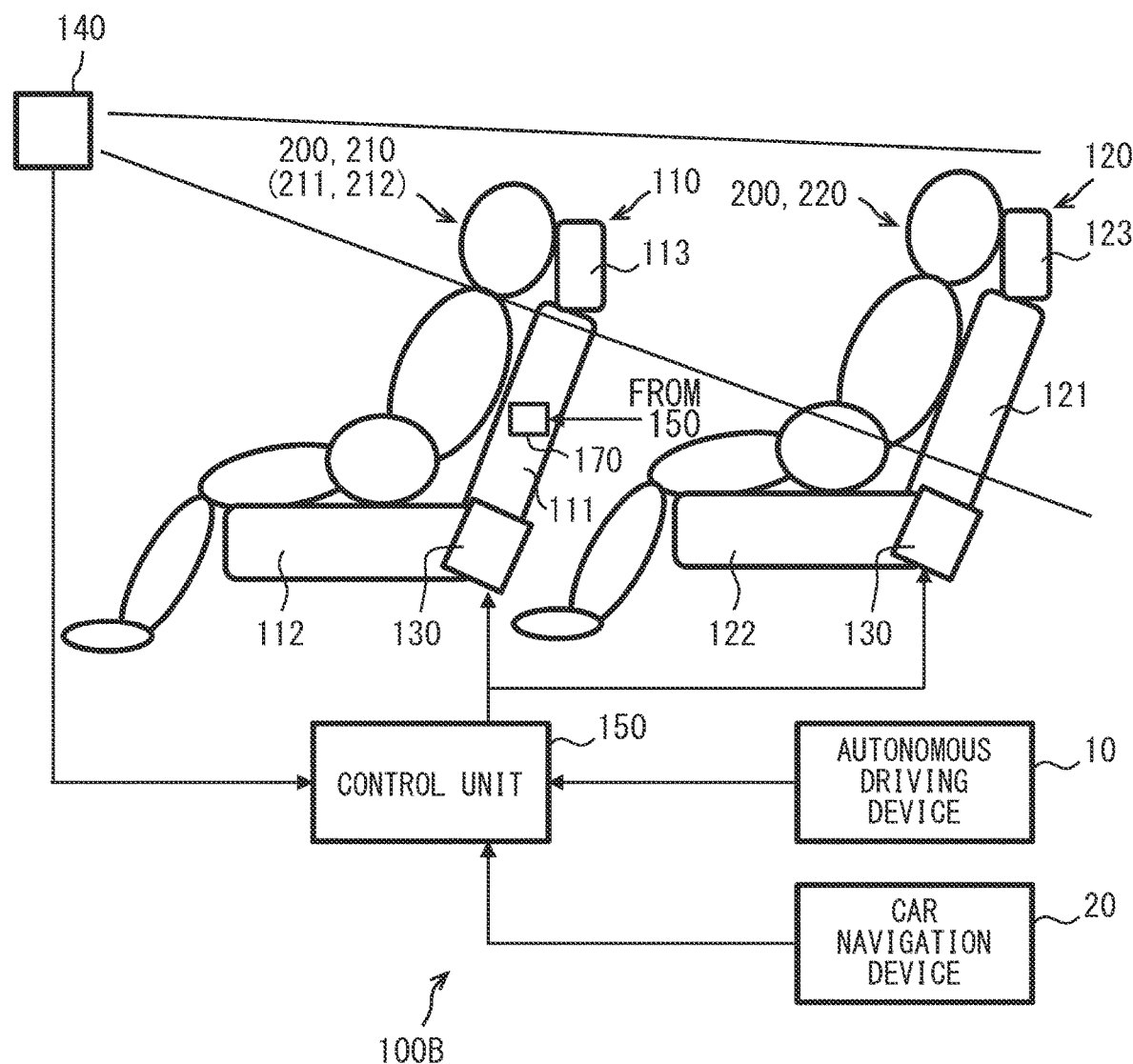
FIG. 13 is an explanatory diagram showing a seat reclining position control device according to an eighth embodiment.

FIG. 13 shows a seat reclining position control device 100B according to the eighth embodiment. The seat reclining position control device 100B includes an awakening unit 170 for awakening the sleeping occupant 200. The awakening unit 170 can be, for example, a vibration generator that generates vibrations to the sleeping occupant 200, a volume adjuster that increases the volume of an audio device, or the like. When the awakening unit 170 is set as a vibration generator, the awakening unit 170 is provided, for example, in the backrest 111 as shown in FIG. 13. When the awakening unit 170 is set as a volume adjuster, the awakening unit 170 is provided, for example, in an audio device.

If the sleeping occupant 200 is the driver 211 and the vehicle is automatically traveling, the control unit 150 controls the seat angle for the driver 211 and helps for awakening the driver 211 when the time until the end of the automatic driving becomes shorter than a predetermined time, for example, using the above-described vibration generator of volume adjuster (awakening unit 170).

As a result, when the driver 211 is sleeping during automatic driving, the driver 211 can be awakened before the automatic driving ends, and the automatic driving can be transitioned smoothly to the manual driving by the driver 211.

Ninth Embodiment

Figure 14:
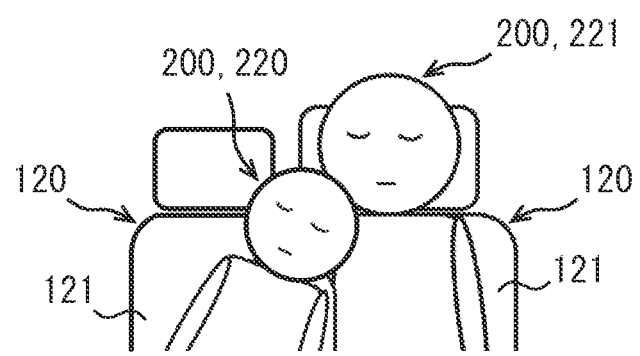
FIG. 14 is an explanatory diagram showing a passenger in a rear seat and another adjacent passenger in a ninth embodiment.

FIG. 14 shows the seat angle control in the ninth embodiment. The configuration of the seat reclining position control device 100 is the same as that of the first embodiment. In the ninth embodiment, when the control unit 150 detects the sleeping occupant 200 and an adjacent occupant 221 adjacent to the sleeping occupant 200, the control unit 150 performs the seat angle control for the sleeping occupant 200 and the adjacent occupant 221 in the same manner.

In this embodiment, the sleeping occupant 200 is a rear seat occupant 220 (for example, a child) seated in the center of the rear seat 120, and the adjacent occupant 221 (for example, a parent) is seated next to the rear seat occupant 220.

When the adjacent occupant 221 is in a sleep state as well as the rear seat occupant 220, the control unit 150 sets the angle of the backrest 121 of the adjacent occupant 221 to be the same as the angle of the backrest 121 of the rear seat occupant 220. When the adjacent occupant 221 is not sleeping, the control unit 150 may set the angle of the backrest 121 of the adjacent occupant 221 to be smaller than the angle of the backrest 121 of the rear seat occupant 220.

As a result, the backrest 121 for the adjacent occupant 221 can be reclined in the same manner as for the rear seat occupant 220, thereby reducing the occurrence of a step between the backrests 121, so as to improve convenience (by reducing discomfort).

Tenth Embodiment

In the tenth embodiment, when the seat angle control is performed for the sleeping occupant 200, the reclining angle is returned to the original setting according to the navigation information from the car navigation device 20. The configuration of the seat reclining position control device 100 is the same as that of the first embodiment.

The navigation information may indicate that the vehicle will reach a predetermined highlight point (such as a scenic point on the way, a famous place, or the destination itself) when the vehicle is being guided to the destination. When this navigation information is obtained, the control unit 150 restores the angle of the backrest 111 or the backrest 121 for the occupant 200 by cancelling the seat angle control.

As a result, it is possible to wake up the occupant 200 and prevent from overlooking the highlight points during the driving by returning the backrest 111, 121 to the normal position.

Eleventh Embodiment

In the eleventh embodiment, the control unit 150 prohibits the seat angle control when the occupant 200 has already changed the angle of the backrest 111 or the backrest 121 while detecting that the occupant 200 is in a sleep state. The configuration of the seat reclining position control device 100 is the same as that of the first embodiment.

If the occupant 200 himself/herself changes the angle of the backrest 111 or the backrest 121, the angle is likely to be the angle that the occupant 200 prefers. Therefore, by prohibiting the seat angle control, the angle set by the occupant 200 can be maintained.

OTHER EMBODIMENT

In the embodiments, the relationship between the front seat occupant 210 and the rear seat occupant 220 is described using the front seat 110 and the rear seat 120 in the seat angle control. However, for example, when a vehicle has three rows of seats, such as a minivan, it is possible to use the second row of seats as the front seat 110 and the third row of seats as the rear seat 120.

In the embodiments, the camera 140 is used as the sleep state detection unit, but is not limited to this. The sleep state detection unit may be a biosensor to detect the sleeping state from the heartbeat, pulse rate, or the like of the occupant 200.

In the embodiments, the camera 140 for detecting the sleep state is also used as the vehicle interior detection unit, but a dedicated camera may be used.

The control unit and the techniques thereof according to the present disclosure may be implemented by one or more special-purposed computers. Such a special-purposed computer may be provided by configuring a processor and a memory programmed to execute one or more functions embodied by a computer program.

Alternatively, the control unit or the method disclosed may be provided by a dedicated computer which includes at least one processor configured by at least one dedicated hardware logic circuits.

Alternatively, the control unit and the like and the method thereof described in the present disclosure may be achieved by one or more dedicated computers constituted by a combination of a processor and a memory programmed to execute one or a plurality of functions and a processor constituted by one or more hardware logic circuits.

The computer program may be stored in a computer-readable non-transition tangible storage medium as an instruction executed by a computer.

Although the present disclosure has been described in accordance with the embodiments, it is understood that the present disclosure is not limited to such embodiments or structures. The present disclosure also encompasses various modifications and variations within the scope of equivalents. In addition, while the various elements are shown in various combinations and configurations, which are exemplary, other combinations and configurations, including more, less or only a single element, are also within the spirit and scope of the present disclosure.

What is claimed is:

1. A seat reclining position control device comprising:
a seat on which an occupant of a vehicle sits;
an adjustment unit configured to adjust an angle of a backrest of the seat;
a sleep state detection unit configured to detect a sleep state of the occupant;
a control unit configured to operate the adjustment unit to control the angle; and
a vehicle interior detection unit configured to detect a vehicle interior state of the vehicle, wherein
the control unit implements a seat angle control to adjust the angle of the backrest for the occupant in a sleep state based on the vehicle interior state to a sleeping angle suitable for sleeping when the sleep state detection unit detects that the occupant is in the sleep state, and
the vehicle is provided with an autonomous driving device that enables an automatic driving, and a car navigation device that grasps a position of the vehicle and performs a destination guidance,
in response to determining that the vehicle is traveling automatically and in response to determining that a time required to reach a destination by the destination guidance is shorter than a predetermined time, the control unit prohibits an execution of the seat angle control for a driver and permits an execution of the seat angle control for a passenger other than the driver.

2. The seat reclining position control device according to claim 1, wherein
the control unit obtains a posture of the occupant in the sleep state as the vehicle interior state, and
the control unit implements the seat angle control when the occupant is not separated from the backrest.

3. The seat reclining position control device according to claim 1, wherein
the adjustment unit is able to adjust a position of a seat portion of the seat, and
the control unit implements the seat angle control and moves the position of the seat portion rearward and downward when there is no passenger in a rear seat at a rear of the occupant in the sleep state as the vehicle interior state.

4. The seat reclining position control device according to claim 1, wherein
when another occupant is in a rear seat at a rear of the occupant in the sleep state as the vehicle interior state, the control unit reduces the angle to be smaller than the sleeping angle for the occupant in the sleep state in performing the seat angle control.

5. The seat reclining position control device according to claim 1, wherein
when another occupant is in a rear seat at a rear of the occupant in the sleep state as the vehicle interior state, the control unit implements the seat angle control for the occupant in the sleep state and reclines a rear seatback of the rear seat.

6. The seat reclining position control device according to claim 1, wherein in response to determining that the vehicle is traveling automatically along a road with a predetermined driving difficulty level, the control unit prohibits the execution of the seat angle control for the driver and permits the execution of the seat angle control for the passenger other than the driver.

7. The seat reclining position control device according to claim 1, further comprising: a notification unit configured to notify the occupant, wherein in case where another occupant is in a rear seat at a rear of the occupant in the sleep state in performing the seat angle control, when the another occupant is awake, the control unit controls the notification unit to notify the another occupant that the seat angle control will be performed in advance, and when the another occupant is in a sleeping state, the control unit prohibits the notification unit from notifying the another occupant.

8. The seat reclining position control device according to claim 1, further comprising:

an awakening unit configured to awaken the occupant in the sleep state, in case where the occupant in the sleep state is the driver, the control unit implements the seat angle control for the driver when the vehicle is automatically traveling, and the control unit activates the awakening unit when a time until an end of the automatic driving becomes shorter than a predetermined time.

9. The seat reclining position control device according to claim 1, wherein when the control unit detects the occupant in the sleep state and an adjacent occupant adjacent to the occupant in the sleep state, the control unit implements the seat angle control for both of the occupant in the sleep state and the adjacent occupant.

10. The seat reclining position control device according to claim 1, wherein after the seat angle control is implemented for the occupant in the sleep state, the control unit restores the angle to an original setting before the vehicle reaches a predetermined highlight point.

11. The seat reclining position control device according to claim 1, wherein the control unit prohibits an execution of the seat angle control when the angle has already been changed by the occupant even while detecting the occupant in the sleep state.

12. A seat reclining position control device comprising:
a computer including a processor and a memory that stores instructions configured to, when executed by the processor, cause the processor to receive at least one of a sleep state of an occupant of a vehicle or a vehicle interior state of the vehicle from a camera, and implement a seat angle control to adjust an angle of a seat for the occupant in a sleep state based on the sleep state or/and the vehicle interior state, wherein the processor prohibits an execution of the seat angle control for a driver and permits an execution of the seat angle control for a passenger other than the driver, in response to an autonomous driving device causing the vehicle to travel automatically and a car navigation device determining that a time required for the vehicle to reach a destination is shorter than a predetermined time.

13. The seat reclining position control device according to claim 12, wherein the processor prohibits the execution of the seat angle control for the driver and permits the execution of the seat angle control for the passenger other than the driver, in response to the autonomous driving device causing the vehicle to travel automatically along a road with a predetermined driving difficulty level.

14. The seat reclining position control device according to claim 12, wherein the processor implements the seat angle control for the driver of the vehicle that is the occupant in the sleep state when the autonomous driving device causes the vehicle to travel automatically, and the processor activates an awakening unit configured to awaken the occupant in the sleep state when a time until an end of automatic driving becomes shorter than a predetermined time.

15. The seat reclining position control device according to claim 12, wherein after the seat angle control is implemented for the occupant in the sleep state, the processor restores the angle to an original setting before the vehicle reaches a predetermined highlight point while the car navigation device performs a destination guidance.

16. The seat reclining position control device according to claim 12, wherein the processor prohibits an execution of the seat angle control when the angle has already been changed by the occupant even while detecting the occupant in the sleep state.

17. The seat reclining position control device according to claim 12, wherein the processor implements the seat angle control and moves a position of a seat portion of the seat rearward and downward when there is no passenger in a rear seat at a rear of the occupant in the sleep state as the vehicle interior state.

18. The seat reclining position control device according to claim 12, wherein when detecting another occupant in a rear seat at a rear of the occupant in the sleep state as the vehicle interior state, the processor reduces the angle to be smaller than a sleeping angle for the occupant in the sleep state in performing the seat angle control.

19. The seat reclining position control device according to claim 12, wherein when detecting another occupant in a rear seat at a rear of the occupant in the sleep state as the vehicle interior state, the processor implements the seat angle control for the occupant in the sleep state and reclines a rear seatback of the rear seat.

* * * * *